(12) United States Patent
Brickl et al.

(10) Patent No.: US 9,782,365 B2
(45) Date of Patent: Oct. 10, 2017

(54) SOLID AMBROXOL-CONTAINING PREPARATION

(75) Inventors: Rolf-Stefan Brickl, Warthausen (DE); Herrad-Odilia Krenkel, Gau-Algesheim (DE)

(73) Assignee: Sanofi-Aventis Deutschland GmbH, Paris (FR)

( * ) Notice: Subject to any disclaimer, the term of this patent is extended or adjusted under 35 U.S.C. 154(b) by 335 days.

(21) Appl. No.: 14/006,183

(22) PCT Filed: Mar. 15, 2012

(86) PCT No.: PCT/EP2012/054615
§ 371 (c)(1),
(2), (4) Date: Dec. 18, 2013

(87) PCT Pub. No.: WO2012/126813
PCT Pub. Date: Sep. 27, 2012

(65) Prior Publication Data
US 2014/0094523 A1    Apr. 3, 2014

(30) Foreign Application Priority Data
Mar. 21, 2011   (EP) .................................. 11159031

(51) Int. Cl.
*A61K 31/137* (2006.01)
*A61K 9/16* (2006.01)

(52) U.S. Cl.
CPC .......... *A61K 31/137* (2013.01); *A61K 9/1617* (2013.01); *A61K 9/1694* (2013.01)

(58) Field of Classification Search
CPC .................................................. A61K 31/137
USPC ........................................................ 514/655
See application file for complete search history.

(56) References Cited

U.S. PATENT DOCUMENTS

| | | | | |
|---|---|---|---|---|
| 5,939,099 A | * | 8/1999 | Grabowski | A61K 9/2054 |
| | | | | 424/488 |
| 2005/0266058 A1 | * | 12/2005 | Esperester | A61K 31/137 |
| | | | | 424/448 |

FOREIGN PATENT DOCUMENTS

| | | | |
|---|---|---|---|
| EP | 0208144 A1 | * | 1/1987 |
| JP | 2000026316 A | | 1/2000 |
| JP | 2000086502 A | | 3/2000 |
| JP | 2004024686 A | | 1/2004 |
| JP | 2005055590 A | | 3/2005 |
| JP | 2008509193 A | | 3/2008 |
| WO | 03030877 A1 | | 4/2003 |
| WO | 2006015943 A2 | | 2/2006 |

OTHER PUBLICATIONS

International Search Report for PCT/EP2012/054615 mailed May 21, 2012.
Abstract in English for EP208144, publication date Jan. 14, 1987.
Abstract in English for JP 2000-026316, publication date Jan. 25, 2000.
Abstract in English for JP 2000-086502, publication date Mar. 28, 2000.
Abstract in English for JP 2004-024686, publication date Jan. 29, 2004.
Database WIPI, "Manufacturing Method for Pharmaceutical Wax Matrix." Thomson Scientific, London, GB, AN-2004-286857.

* cited by examiner

*Primary Examiner* — Jennifer M Kim
(74) *Attorney, Agent, or Firm* — Edell, Shapiro & Finnan, LLC

(57) ABSTRACT

The present invention relates to solid preparations containing ambroxol which are obtainable by melt extrusion of the mixture consisting of a) 30 to 80% by weight of ambroxol hydrochloride, b) 2 to 68% by weight of at least one hydrogenated vegetable oil, c) 2 to 68% by weight of at least one mixture containing fatty acid ester and/or hydroxy fatty acid ester and d) 0 to 66% by weight of one or more pharmaceutical adjuvants, based in each case on the total amount of the preparation and its use for secretolytic treatment in acute and chronic bronchopulmonary diseases.

5 Claims, 3 Drawing Sheets

SOLID AMBROXOL-CONTAINING PREPARATION

FIELD OF THE INVENTION

The present invention relates to solid preparations containing ambroxol which may be obtained by joint melt extrusion and their use for the secretolytic treatment of acute and chronic bronchopulmonary diseases.

BACKGROUND OF THE INVENTION

Ambroxol hydrochloride (trans-4-(2-amino-3,5-dibromobenzylamino)-cyclohexanol hydrochloride) is an active substance from the category of expectorants, which is used in the treatment of acute and chronic diseases of the lower respiratory tract that are associated with disorders of the formation and transport of mucus, and is used for the relief of acute sore throats. Ambroxol hydrochloride is used in various formulations, for example as tablets for sucking, drops, syrup, tablets, delayed-release capsules, effervescent tablets or inhalable concentrate.

The commercially obtainable solid preparations of ambroxol usually consist of pellets produced by spray hardening and having an active substance content of about 35% by weight.

A disadvantage of this production method is the high dependency of the release of active substance on the particle size distribution, which in turn is strongly dependent on the spray parameters. This requires considerable effort to ensure the reproducibility of the release of active substance. Another disadvantage of the production method is the low content of active substance that can be achieved in the solid preparation, which is usually less than 35% as a result of spraying problems.

SUMMARY OF THE INVENTION

The problem of the present invention was to provide solid preparations containing ambroxol which can be prepared by a reproducible method and allow the release of active substance to be adjusted in a controlled manner. The production process for this preparation should preferably be simple, robust and suitable for continuous production.

A further problem of the present invention was to provide solid pharmaceutical preparations with a high content of active substance, the release characteristics of which can be adjusted in controlled manner in order to readily achieve bioequivalence to the commercially available solid preparations as necessary.

These problems are solved by solid preparations containing ambroxol which are obtainable by melt extrusion of a mixture consisting of a) 30 to 80% by weight of ambroxol hydrochloride, b) 2 to 68% by weight of at least one hydrogenated vegetable oil, c) 2 to 68% by weight of at least one mixture containing fatty acid ester and/or hydroxy fatty acid ester and d) 0 to 66% by weight of one or more pharmaceutical adjuvants, based in each case on the total amount of preparation.

Accordingly, the present invention relates to the ambroxol-containing preparations described, a method for preparing them, pharmaceutical formulations containing the preparations according to the invention and the use of the compositions according to the invention for secretolytic treatment in acute and chronic bronchopulmonary diseases.

According to the invention, ambroxol hydrochloride is used as component a). It does not decompose under the processing conditions of melt extrusion according to the invention.

DETAILED DESCRIPTION OF THE INVENTION

Figure 1:
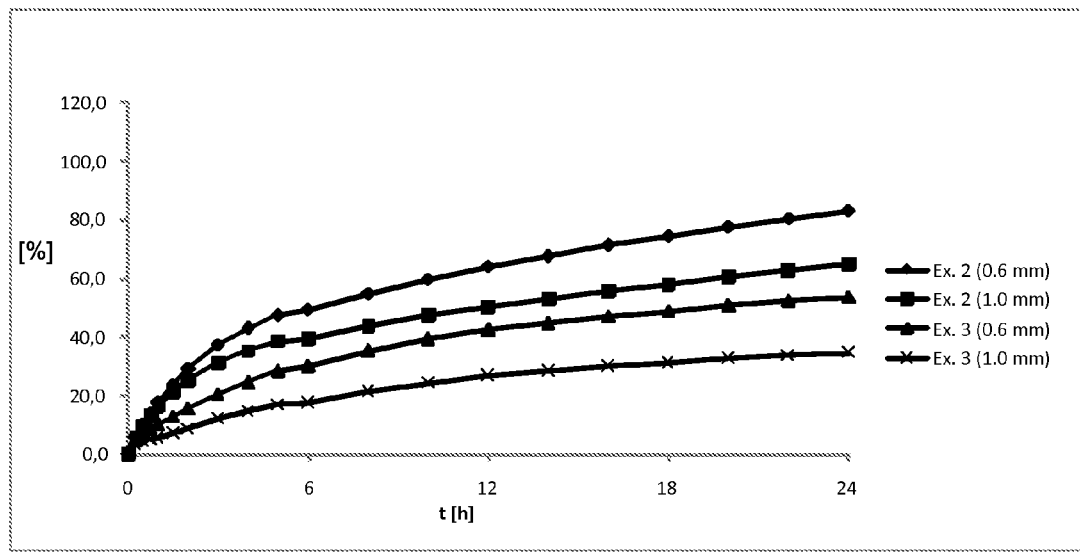
FIG. 1 shows the influence of the carnauba wax content on the release of active substance and the influence of the particle size of the extruded material. The release of the active substance is plotted in [%] over time in [h]. The particle diameter of the extruded material of the individual measuring series used is given as "0.6 mm" or "1.0 mm".

As noted above, the present invention relates to solid preparations containing ambroxol which are obtainable by melt extrusion of a mixture consisting of a) 30 to 80% by weight of ambroxol hydrochloride, b) 2 to 68% by weight of at least one hydrogenated vegetable oil, c) 2 to 68% by weight of at least one mixture containing fatty acid ester and/or hydroxy fatty acid ester and d) 0 to 66% by weight of one or more pharmaceutical adjuvants, based in each case on the total amount of preparation.

The quantity of component a) in the preparation according to the invention may vary within wide limits depending on the desired rate of release. Thus, the ambroxol content will usually be in the range from 30 to 80% by weight, preferably in the range from 40 to 80% by weight. One particular embodiment of the present invention relates to preparations with an ambroxol content in the range from 60 to 80% by weight, preferably 70 to 80% by weight and especially 75 to 79% by weight. Surprisingly, it has been found that, with the preparations according to the invention, a release profile equivalent to the commercial preparations with a low active substance content can be obtained, in spite of a high ambroxol content.

The particle size of the ambroxol hydrochloride used in the preparations according to the invention is non-critical within wide limits. The selected particle size may be used for fine adjustment of the desired release profile. Basically, release is delayed further, the larger the particle size.

As component b) the preparations according to the invention contain at least one hydrogenated vegetable oil.

The preparations according to the invention contain components b) usually in an amount of 2 to 68% by weight, preferably in an amount of 4 to 30% by weight and most preferably in an amount of 5 to 20% by weight, based in each case on the total weight of the preparation.

Suitable hydrogenated vegetable oils b) usually have a melting point of at least 50° C. The melting point of the hydrogenated vegetable oils or mixtures thereof may be for example in the range from 50 to 100° C., preferably 60 to 95° C., particularly preferably in the range from 70 to 90° C. This ensures the extrudability of the preparation.

Examples of suitable hydrogenated vegetable oils b) include hardened castor oil (hydrogenated castor oil), hydrogenated palm kernel oil, hydrogenated palm oil, hardened coconut glycerides, hydrogenated coconut oil or hydrogenated jojoba oil and mixtures thereof. Preferably, hydrogenated castor oil is used as component b) in the preparations according to the invention.

As components c) the preparations according to the invention contain at least one mixture comprising fatty acid ester and/or hydroxy fatty acid ester.

Suitable mixtures c) containing fatty acid ester and/or hydroxy fatty acid ester usually have a melting point of at least 45° C. The melting point of the mixtures c) containing fatty acid ester and/or hydroxy fatty acid ester is for example in the range from 45 to 95° C., preferably 55 to 90° C., particularly preferably in the range from 65 to 85° C. This guarantees the extrudability of the preparation.

Examples of suitable mixtures c) containing fatty acid esters and/or hydroxy fatty acid esters include carnauba wax, candelilla wax, Japan tallow or rice bran wax and mixtures thereof. Preferably, carnauba wax is used as component c) in the preparations according to the invention.

The preparations according to the invention contain component c) usually in an amount of 2 to 68% by weight, preferably in an amount of 5 to 30% by weight and particularly preferably in an amount of 5 to 20% by weight, based in each case on the total weight of the preparation.

The total amount of components b) and c) in the preparations according to the invention is usually from 10 to 70% by weight, preferably from 12 to 40% by weight, particularly preferably from 14 to 30% by weight and most particularly preferably from 15 to 25% by weight, based in each case on the total weight of the preparation.

Within the limits specified, the amount of component b) relative to the amount of component c) preferably depends on the desired release profile. Usually, the ratio of the amounts of b) to c) is in a range from 10:1 to 1:10, preferably in the range from 5:1 to 1:5.

The particle size of the components b) and c) used in the preparations according to the invention is non-critical within wide limits.

As component d), the preparations according to the invention may contain conventional pharmaceutical adjuvants such as disintegrants, fillers, lubricants, separating agents, flow regulators, plasticizers and colourings in amounts of up to 66% by weight, preferably 0 to 36% by weight, particularly preferably 0 to 5% by weight and most particularly preferably 0 to 3% by weight. These amounts and those specified hereinafter relate in each case to the total weight of the preparation.

Examples of suitable disintegrants include crospovidone, croscarmellose, sodium alginate, sodium starch glycolate, carboxymethyl sodium starch glycolate, dried maize starch and mixtures thereof, while the amount of disintegrant, if used, is normally in the range from 0.01 to 50% by weight, preferably 0.05 to 20% by weight and particularly preferably in the range from 0.1 to 10% by weight.

Examples of suitable fillers include the oxides of magnesium, aluminium, silicon and titanium as well as lactose, mannitol, sorbitol, xylitol, pentaerythritol and the derivatives thereof, while the amount of filler, if used, is normally in the range from 0.01 to 5, preferably 0.05 to 2% by weight and particularly preferably in the range from 0.1 to 1% by weight.

Examples of suitable flow regulators include waxes such as lecithins, mono-, di- and triglycerides of long-chain fatty acids, such as $C_{12}$-, $C_{14}$-, $C_{16}$- and $C_{18}$-fatty acids, while the amount, if used, is normally in the range from 0.01 to 5, preferably 0.05 to 2% by weight and particularly preferably in the range from 0.1 to 1% by weight.

Examples of suitable plasticizers include, besides low-molecular polyalkylene oxides such as polyethyleneglycol, polypropylene glycol and polyethylene proplylene glycol, polyhydric alcohols such as propylene glycol, glycerol, penataerythritol and sorbitol as well as sodium diethyl sulphosuccinate, mono-, di- and triacetate of glycerol and polyethylene glycol stearic acid esters, while the quantity of plasticizers, if used, is normally in the range from 0.01 to 5, preferably 0.05 to 2% by weight and particularly preferably in the range from 0.1 to 1% by weight.

Examples of suitable lubricants include long-chain alcohols such as stearyl alcohol, stearates of aluminium or calcium as well as talc and silicons, while the amount of lubricant, if used, is usually in the range from 0.01 to 50% by weight, preferably 0.05 to 20% by weight and particularly preferably in the range from 0.1 to 10% by weight.

In another aspect the invention relates to a method for producing the preparations according to the invention, in which a mixture of a) ambroxol hydrochloride, b) the hydrogenated vegetable oil, c) the mixture containing fatty acid ester and/or hydroxy fatty acid ester and d) optionally the adjuvants is prepared and further processed by melt extrusion.

The extrusion of melts containing active substance is described for example in EP 0809487, EP 0809488, EP 0854707 or EP 0998919.

In order to prepare the preparations according to the invention, ambroxol hydrochloride in the form of a physical mixture with the other components b), c) and d) can be extruded, while the mixing of components a) to d) may take place before and/or during the extrusion process. Usually, the separated components a) to d) will be added to the extruder simultaneously and mixed in during the extrusion process.

Moreover, the extrusion of all the components takes place in a manner known per se in extruders, preferably in single- or twin-screw extruders in a temperature range between 40 and 80° C., preferably 60 to 75° C. The shaping of the ambroxol-containing melt to form the preparations according to the invention may be carried out for example using nozzle plates with corresponding bores. The comminution of the extruded material into pieces of equal volume may either be carried out with rotating blades directly on the nozzle plate or the extruded strings, after hardening, may be ground up in suitable mils (e.g. Comill with rasping sieve) or broken up in spheronizers. The extruded pieces can be further used directly or may be rounded in spheronizers at temperatures of between 40 and 80° C., preferably at 50 to 65° C., in order to improve their flow characteristics.

The extruded materials thus obtained may either be administered directly in loose form, i.e. as pellets or granules, using metering systems, or transferred into capsules or combined with tabletting adjuvants and compressed in conventional tablet-making machines to form tablets.

The preparations according to the invention and the formulations produced from them are pharmaceutical formulations with delayed release of the active substance.

If desired, the solid preparation or pharmaceutical formulation according to the invention may be provided with a conventional coating to improve the appearance and/or flavour or to delaying the release of active substance further. The present invention provides a simple way of adjusting the active substance release profile of the pharmaceutical formulation according to the invention, particularly when producing pharmaceutical formulations with a delayed release of active substance.

The invention is hereinafter explained more fully by reference to non-restrictive examples.

EXAMPLE OF EMBODIMENTS

Examples 1-6

TABLE 1

Composition of examples 1-6:

| Ex. | Ambroxol Hydrochloride (mg) | Hydrogenated Castor oil (mg) | Carnauba Wax (mg) | Stearyl Alcohol (mg) | Collidone CL (% by weight) | Ambroxol Hydrochloride (% by weight) |
|---|---|---|---|---|---|---|
| 1 | 30 | 6 | 2 | — | — | 79 |
| 2 | 60 | 12 | 4 | 4 | — | 75 |
| 3 | 60 | 4 | 12 | 4 | — | 75 |
| 4 | 60 | 12 | 4 | 4 | 4 | 71 |
| 5 | 60 | 12 | 4 | 4 | — | 75 |
| 6 | 60 | 12 | 4 | 4 | — | 75 |

The amounts of ambroxol hydrochloride and components b), particularly hydrogenated castor oil with a nominal melting point of 80° C., c), particularly carnauba wax and d), particularly stearyl alcohol and collidone CL, specified in Table 1, were mixed together, placed in a co-rotating 9 mm twin screw extruder (of the type made by Messrs Three-Tech, Switzerland) and extruded at a barrel temperature of 78° C. The nozzle diameters used were 0.6 mm and 1.0 mm. The extruded strings emerging through the extruder nozzle were pelleted by means of a mill with a rasping sieve, ground up and packed into hard gelatine capsules with a capacity of 75 mg of active substance. For Examples 1 and 4, jet-milled active substance with a particularly small particle size was used, while for Examples 2, 3, 5 and 6, rather coarser pin-milled active substance was used.

The release of active substance was measured in a Sotax dissolution apparatus type AT7 by the paddle method at 100 rpm in phosphate buffer pH 7.5 at 37° C. for 24 hours. This in vitro method is used to determine the dissolution rate of preparations containing active substance.

Figure 2:
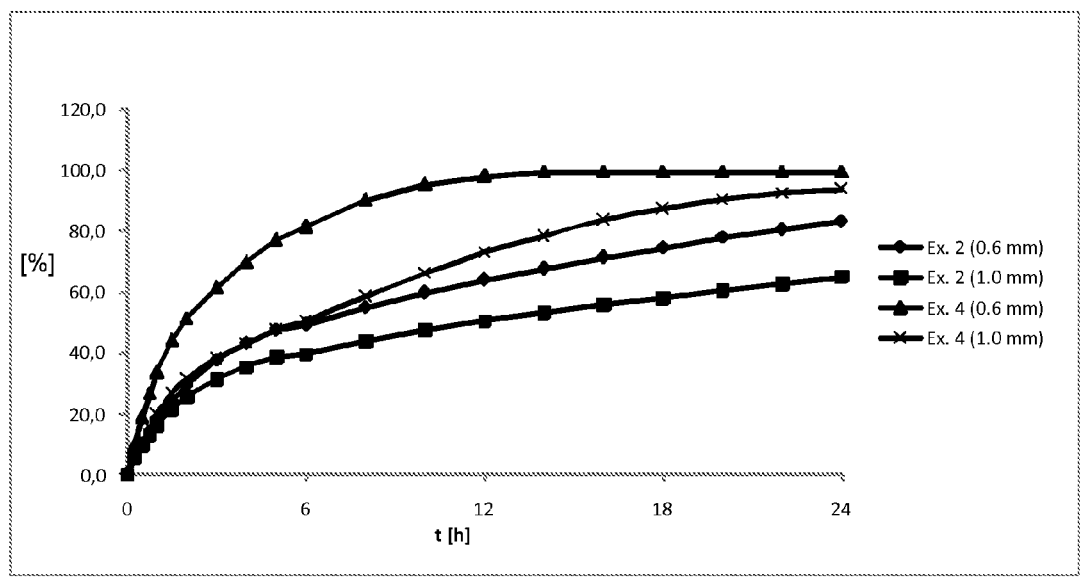
FIG. 2 shows the influence of a disintegrant on the release of active substance and the influence of the particle size of the extruded material. The release of active substance is plotted in [%] over the time in [hours]. The particle diameter of the extruded material of the individual measuring series used is given as "0.6 mm" or "1.0 mm".
Figure 3:
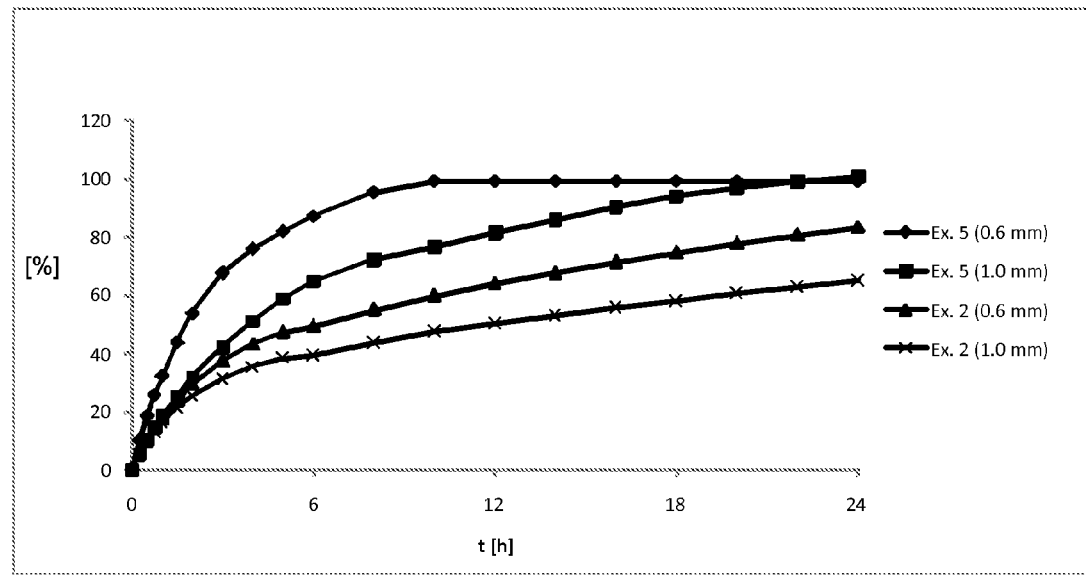
FIG. 3 shows the influence of the particle size of ambroxol hydrochloride on the release of the active substance and the influence of the particle size of the extruded material. The release of active substance is plotted in [%] over the time [hours]. The particle diameter of the extruded material of the individual measuring series used is given as "0.6 mm" or "1.0 mm" in each case.

The results of these tests are shown in FIGS. 1 to 3.

FIG. 1 shows that an increase in the proportion of carnauba wax significantly increases the delay to the release, as does an increase in the diameter of the extruded material.

FIG. 2 shows that the addition of a disintegrant significantly reduces the delay to the release, as does an increase in the diameter of the extruded material.

FIG. 3 shows that a smaller particle size of the ambroxol hydrochloride significantly decreases the delay to the release, as does an increase in the diameter of the extruded material.

Examples 7-10

TABLE 2

Composition of Examples 7-10

| Ex. | Ambroxol Hydrochloride (mg) | Hydrogenated Castor Oil (mg) | Carnauba Wax (mg) | Ambroxol Hydrochloride (% by weight) |
|---|---|---|---|---|
| 7 | 150 | 30 | 10 | 78.9 |
| 8 | 15 | 25 | 15 | 78.9 |
| 9 | 150 | 20 | 20 | 78.9 |
| 10 | 150 | 10 | 30 | 78.9 |

The quantities of jet-milled ambroxol hydrochloride and component b), particularly hydrogenated castor oil with a nominal melting point of 80° C., and component c), particularly carnauba wax, specified in Table 2, were mixed together, placed in a co-rotating 34 mm twin screw extruder (of the type made by Messrs Werner & Pfleiderer) and extruded at a material temperature of 70° C. The nozzle diameters used were 0.7 mm and 0.8 mm. The extruded strings emerging through the extruder nozzle were broken up into rods in a spheroniser at 36° C. and 1000 rpm for a period of five minutes and then spheronised into round pellets at 60° C. and 100 rpm for 20 minutes. Then the rods or pellets were packed into hard gelatine capsules with a capacity of 75 mg of active substance.

The release of active substance was measured in a Sotax dissolution apparatus type AT7 by the paddle method at 100 rpm in phosphate buffer pH 6.8 at 37° C. for a period of 7 hours.

This in vitro method is used to determine the rate of dissolution of preparations containing active substance.

Figure 4:
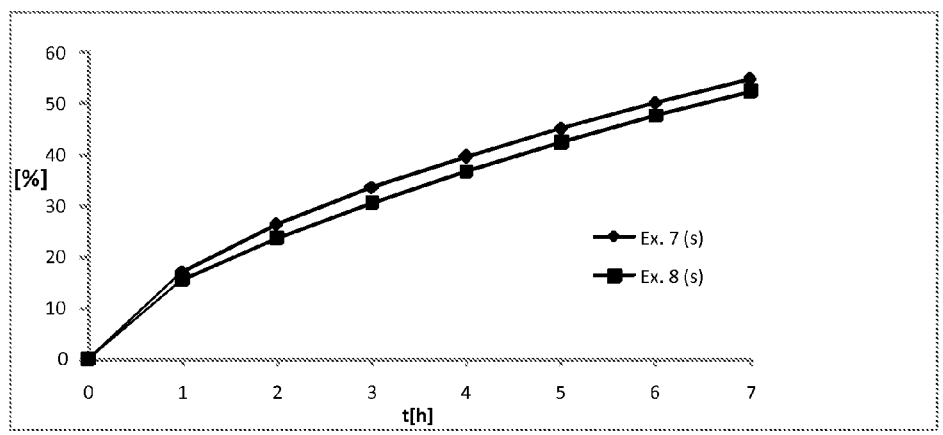
FIG. 4 shows the influence of the content of hydrogenated castor oil and carnauba wax on the release of active substance. The release of active substance is plotted in [%] over the time in [h]. The shape (spheronisation) of the extruded material used is indicated by (s) for rods and (p) for pellets.
Figure 5:
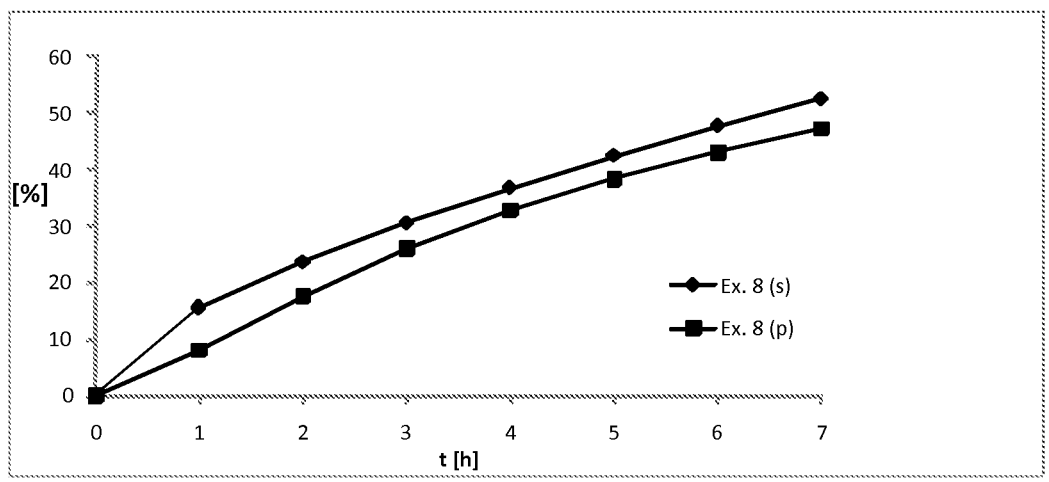
FIG. 5 shows the influence of the spheronisation on the release of active substance. The release of active substance is plotted in [%] over the time in [h]. The shape (spheronisation) of the particular extruded material used is indicated by (s) for rods and (p) for pellets.

The results of this test are shown in FIGS. 4 and 5.

FIG. 4 shows that by varying the ratio of b), especially hydrogenated castor oil, and c), especially carnauba wax, it is readily possible to fine-tune the release of active substance. The compositions according to Examples 7 and 8 used for this purpose were in rod form (s).

FIG. 5 shows that fine tuning of the release of active substance is also readily possible by varying the spheronisation. The compositions according to Example 8 used for this were present both in rod form (s) and in pellet form (p).

These examples show that the release characteristics (release of active substance) can be controlled well over a very wide range, i.e. virtually any desired delay profile can be achieved.

The invention claimed is:

1. A solid formulation containing ambroxol, prepared by the process of melt extrusion of a mixture consisting of a) 70-80% by weight of ambroxol hydrochloride, b) 5-20% by weight of hydrogenated castor oil having a melting point of 70 to 90° C., c) 5-20% by weight of carnauba wax having a melting point of 55 to 90°, and d) 0-5% by weight of one or more pharmaceutical excipients, based in each case on the total amount of the preparation.

2. A method of preparing a solid formulation comprising ambroxol hydrochloride comprising melt extruding a composition consisting of:
   a) 70-80% by weight of ambroxol hydrochloride,
   b) 5-20% by weight of hydrogenated castor oil having a melting point of 70 to 90° C.,
   c) 5-20% by weight of carnauba wax having a melting point of 55 to 90° C., and
   d) 0-5% by weight of one or more pharmaceutical excipients,
   wherein the amount of each of the components a) to d) is based on the total amount of the solid formulation.

3. A pharmaceutical formulation consisting of a) 70-80% by weight of ambroxol hydrochloride, b) 5-20% by weight of hydrogenated castor oil having a melting point of 70 to 90° C., c) 5-20% by weight of carnauba wax having a melting point of 55 to 90° C., and d) 0-5% by weight of one or more pharmaceutical excipients, based in each case on the total amount of the formulation.

4. The pharmaceutical formulation of claim 3, wherein the one or more pharmaceutical excipients comprises stearyl alcohol that is present in the formulation.

5. A method of using the formulation according to claim 3 for secretolytic treatment in acute and chronic bronchopulmonary diseases.

* * * * *